(12) United States Patent
Montebello et al.

(10) Patent No.: US 6,312,375 B1
(45) Date of Patent: Nov. 6, 2001

(54) INFLATABLE COVERING FOR TANDEM COLPOSTAT INTRACAVITARY IMPLANT

(76) Inventors: Joseph F. Montebello, 10241 E. Thompson Rd., Indianapolis, IN (US) 46239; Robert T. Woodburn, III, 11383 Leander La., Indianapolis, IN (US) 46236

( * ) Notice: Subject to any disclaimer, the term of this patent is extended or adjusted under 35 U.S.C. 154(b) by 0 days.

(21) Appl. No.: 09/368,557

(22) Filed: Aug. 5, 1999

Related U.S. Application Data

(60) Provisional application No. 60/095,664, filed on Aug. 7, 1998.

(51) Int. Cl.[7] ............................................. A61N 5/00
(52) U.S. Cl. ............................................. 600/6; 600/3
(58) Field of Search ................... 600/1–3, 6, 7, 600/8; 378/20, 65

(56) References Cited

U.S. PATENT DOCUMENTS

| | | |
|---|---|---|
| 3,807,386 | 4/1974 | Rocoplan et al. . |
| 3,872,856 | 3/1975 | Clayton . |
| 4,292,960 | 10/1981 | Paglione . |
| 4,294,264 | 10/1981 | Fischell et al. . |
| 4,331,131 | 5/1982 | Kumar . |
| 4,434,789 | 3/1984 | Kumar . |
| 5,012,357 | 4/1991 | Schoeppel et al. . |
| 5,295,945 * | 3/1994 | Miller ........................................ 600/6 |
| 5,562,594 * | 10/1996 | Weeks ....................................... 600/3 |
| 5,653,683 | 8/1997 | D'Andrea . |

* cited by examiner

Primary Examiner—John P. Lacyk
Assistant Examiner—Ryan Carter

(57) ABSTRACT

An apparatus for use in optimizing radiation dose distributions to a rectum and a bladder of a patient during the treatment of malignancies of female genitalia is provided in accordance with the present invention. The apparatus includes a colpostat intracavitary implant including a housing portion adapted to receive a radiation source therein and a jacket. The jacket defines a cavity sized to receive the housing portion. The jacket is configured to selectively expand in volumetric size to move the rectum and the bladder away from the radiation source.

20 Claims, 7 Drawing Sheets

INFLATABLE COVERING FOR TANDEM COLPOSTAT INTRACAVITARY IMPLANT

This claims priority under 35 U.S.C. §119(e) of Ser. No. 60/095,664 filed Aug. 7, 1998, and which is incorporated herein by reference.

BACKGROUND AND SUMMARY OF THE INVENTION

The present invention relates to implants, more particularly to intracavitary implants. Most particularly, the present invention relates to intracavitary implants for moving critical structures.

Intracavitary apparatuses for use in radiation procedures are known. See for example U.S. Pat. Nos. 5,653,683 to D's Andrea and 3,872,856 to Clayton.

According to the present invention a dose optimization apparatus is provided. The apparatus comprises a colpostat intracavitary implant that includes a housing portion adapted to receive a radiation source therein and a jacket defining a cavity that is sized to receive the housing. The jacket is configured to selectively expand in volumetric size.

According to another embodiment of the present invention a dose optimization apparatus suitable for use with a colpostat intracavitary implant is provided. The apparatus includes a jacket adapted to surround the housing. In addition, the jacket is configured to selectively expand in volumetric size.

In yet another embodiment of the present invention a method is provided for optimizing radiation dose distributions to a rectum and a bladder of a patient in the treatment of malignancies of female genitalia. The method comprises the steps of providing a tandem, a colpostat, radiation sources, and a jacket, the jacket defining a cavity and being configured to selectively expand in volumetric size, inserting the colpostat into the cavity to form a colpostat/jacket subassembly, inserting the tandem into a vagina of a patient until the tandem passes into a uterus, inserting the colpostat/jacket subassembly into the vagina adjacent to the tandem, inserting at least one radiation source into the tandem and into the colpostat, and inflating the jacket to press the wall of the vagina away from the colpostat and therefore moving the rectum and the bladder away from the radiation sources.

Additional features and advantages of the invention will become apparent to those skilled in the art upon consideration of the following detailed description of a preferred embodiment exemplifying the best mode of carrying out the invention.

BRIEF DESCRIPTION OF THE DRAWINGS

The detailed description particularly refers to the accompanying figures in which.

DETAILED DESCRIPTION OF THE DRAWINGS

Figure 1:
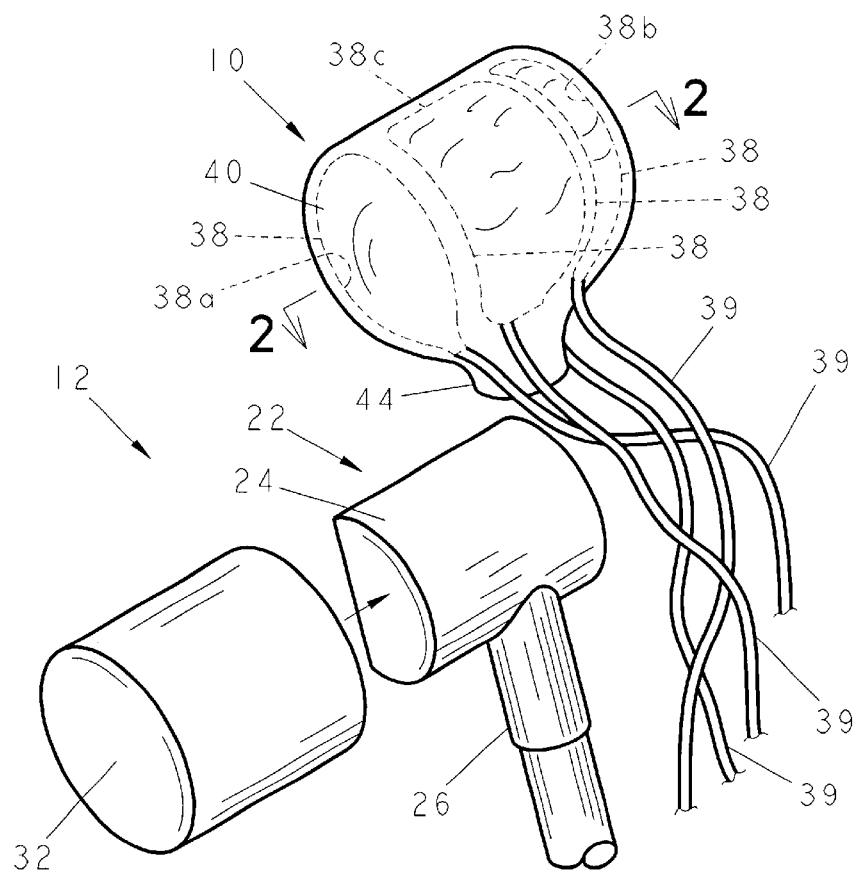
FIG. 1 is an exploded perspective view of a dose optimization apparatus in accordance with the present invention adapted to surround a colpostat intracavitary implant that includes a cap and a colpostat with housing portion selectively positioned in the cap and a stem extending from the housing, the dose optimization apparatus including a jacket defining a cavity, partitions cooperating with the jacket to define a plurality of secondary chambers, and tubes in fluid communication with the secondary chambers.

FIG. 1 illustrates a dose optimization apparatus 10 in accordance with the present invention. Apparatus 10 is adapted to surround a tandem colpostat intracavitary implant 12 for treating malignancies of female genitalia to optimize dose distribution. Apparatus 10 is configured to move critical structures, such as a rectum 14 and a bladder 16 (FIG. 3) further from a radiation source 18 (FIG. 2) housed in implant 12. Apparatus 10 provides a pre-determined radiation distribution, adjusts the relative positioning of implant 12, and increases the percent depth dose to parmetial tissue 13 relative to vagina 34.

Figure 2:
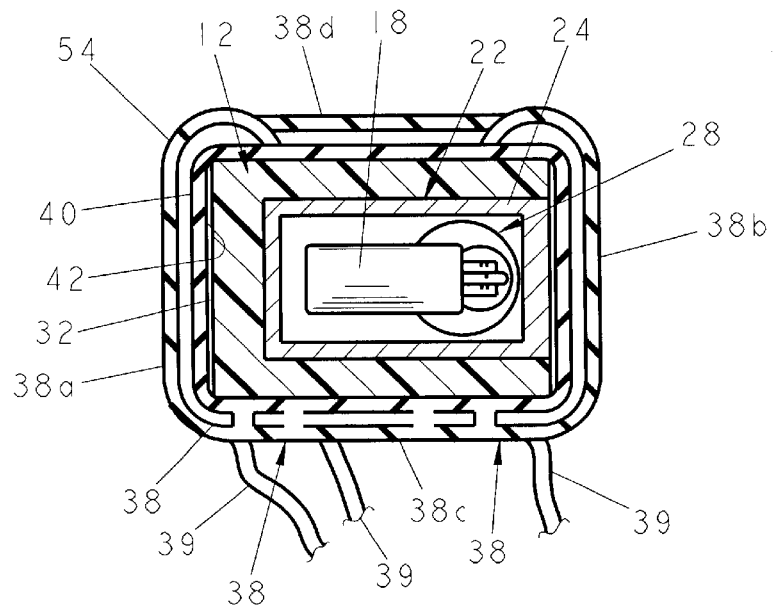
FIG. 2 is a view taken along lines 2—2 of FIG. 1 following assembly of the jacket over the cap and the colpostat showing the radiation source positioned to lie within the housing portion of the colpostat, the colpostat positioned to lie within the cap, and the cap positioned to lie within the cavity of the dose optimization apparatus.
Figure 3:
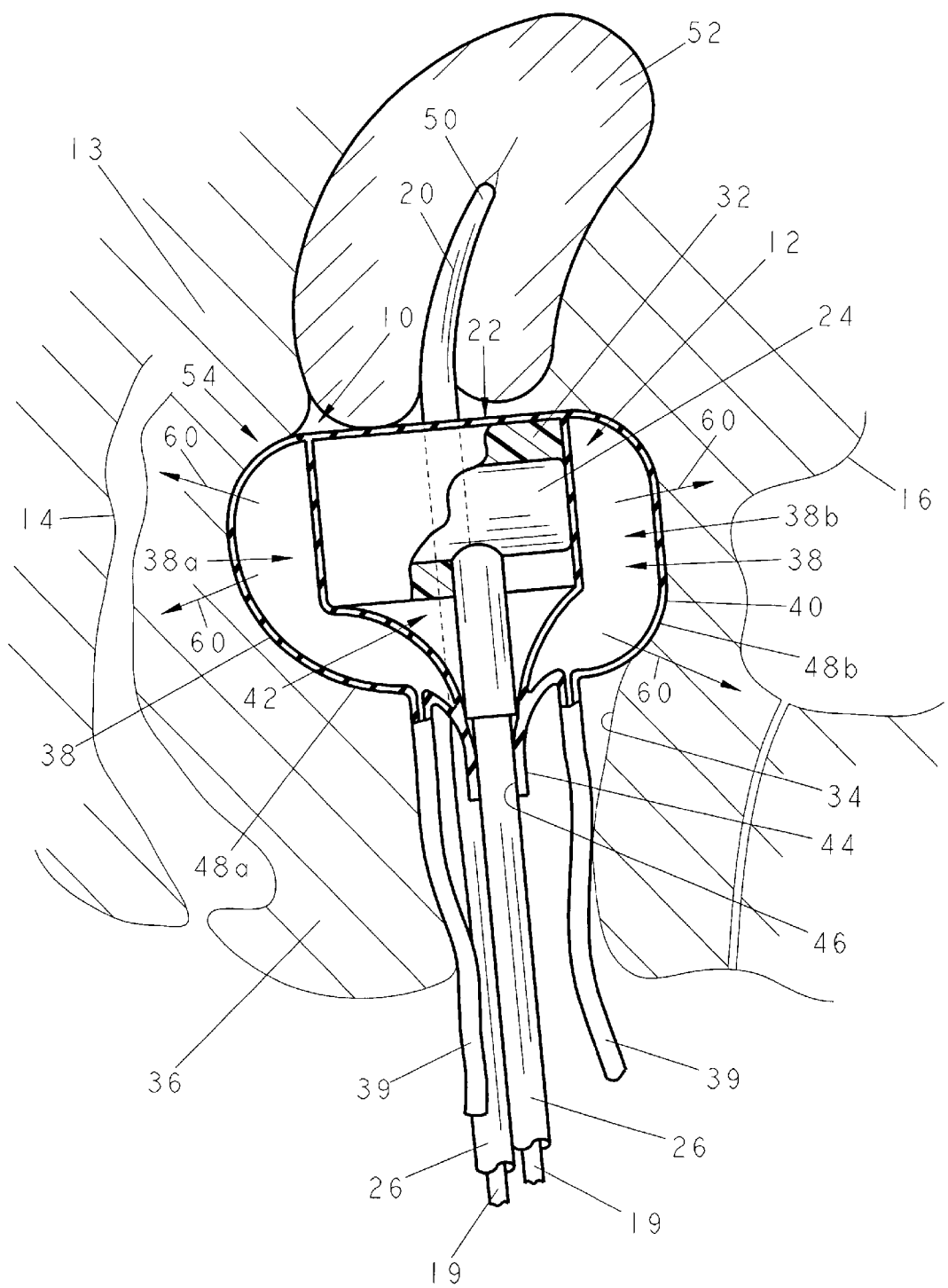
FIG. 3 is a sagittal cross-sectional view of the dose optimization apparatus of FIG. 1 surrounding the colpostat and a tandem positioned to lie within the vagina of a patient and showing each of the secondary chambers of the dose optimization apparatus in an inflated position moving critical structures, such s the rectum and bladder, further from the radiation source housed in the colpostat and providing a pre-determined radiation distribution.
Figure 4:
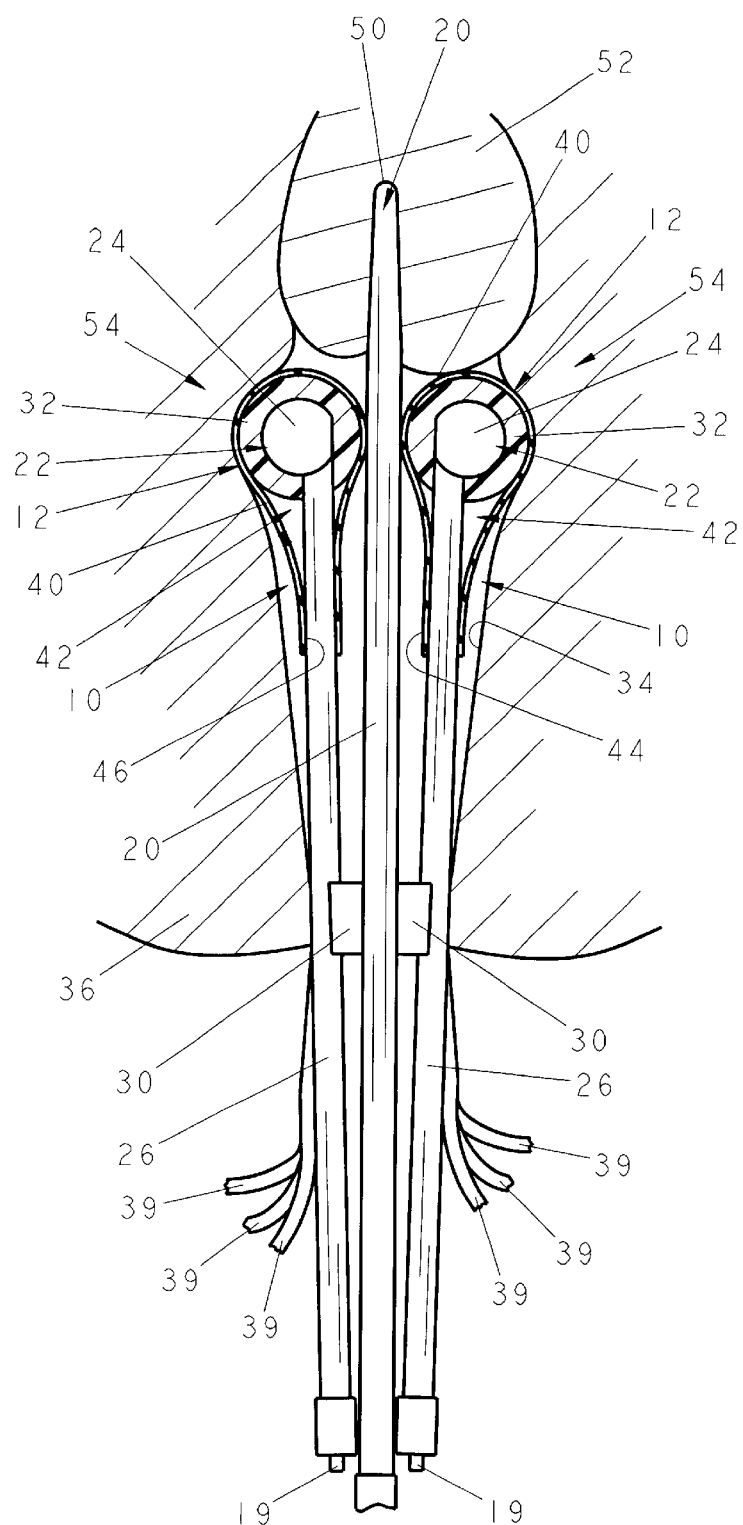
FIG. 4 is a coronal cross-sectional view of a tandem colpostat intracavitary implant including the tandem and two colpostats and two dose optimization apparatuses in accordance with the present invention positioned to lie within the vagina of the patient and showing the secondary chambers in a deflated position.

As shown in FIG. 4, implant 12 includes a tandem 20 and colpostats 22. Colpostats 22 are positioned to lie spaced-apart from one another on opposing sides of tandem 20. Each colpostat 22 includes a generally cylindrical housing portion 24 coupled to a stem 26. Referring now to FIG. 2, housing portion 24 defines a chamber 28 formed to house radiation source 18 therein. Radiation source 18 is coupled to a rod 19, as shown in FIG. 3. In addition, coupling members 30 (FIG. 5) are coupled to stems 26 of colpostats 22 to position colpostats 22 in a generally stationary position relative to tandem 20. Although implant 12 is illustrated and described, it is appreciated that a wide variety of commercially available tandem colpostat intracavitary implants are contemplated for use in accordance with the present invention. It is also appreciated that this disclosure contemplates that apparatus 10 is suitable for use with any number of intracavitary implants for treating malignancies of female genitalia.

As shown in FIG. 1, tandem colpostat intracavitary implant 12 further includes a cap 32 configured to surround housing portion 24. Cap 32 is constructed of a plastic material and is sized to increase a dimension of housing portion 24. Cap 32 is configured to move critical structures, such as rectum 14 and bladder 16 (FIG. 3) an initial pre-determined distance form radiation source 18 positioned within colpostat 22. It is understood that apparatus 10 in accordance with the present invention is suitable for use with implant 12 that may include caps 32 with a variety of shapes and sizes or with implants without caps. See FIGS. 6 and 7.

Apparatus 10 of the present invention cooperates with implant 12 to cover housing portion 24 and cap 32 prior to insertion of implant 12 into a vagina 34 of a patient 36. Apparatus 10 permits the physician to utilize a relatively small colpostat 22, which aids in insertion in vagina 34. Apparatus 10 presses rectum 14 and bladder 16 away from radiation source 18 by inflating selective secondary chambers 38 surrounding colpostat 22, after colpostat 22 has been placed within vagina 34.

Figure 6:
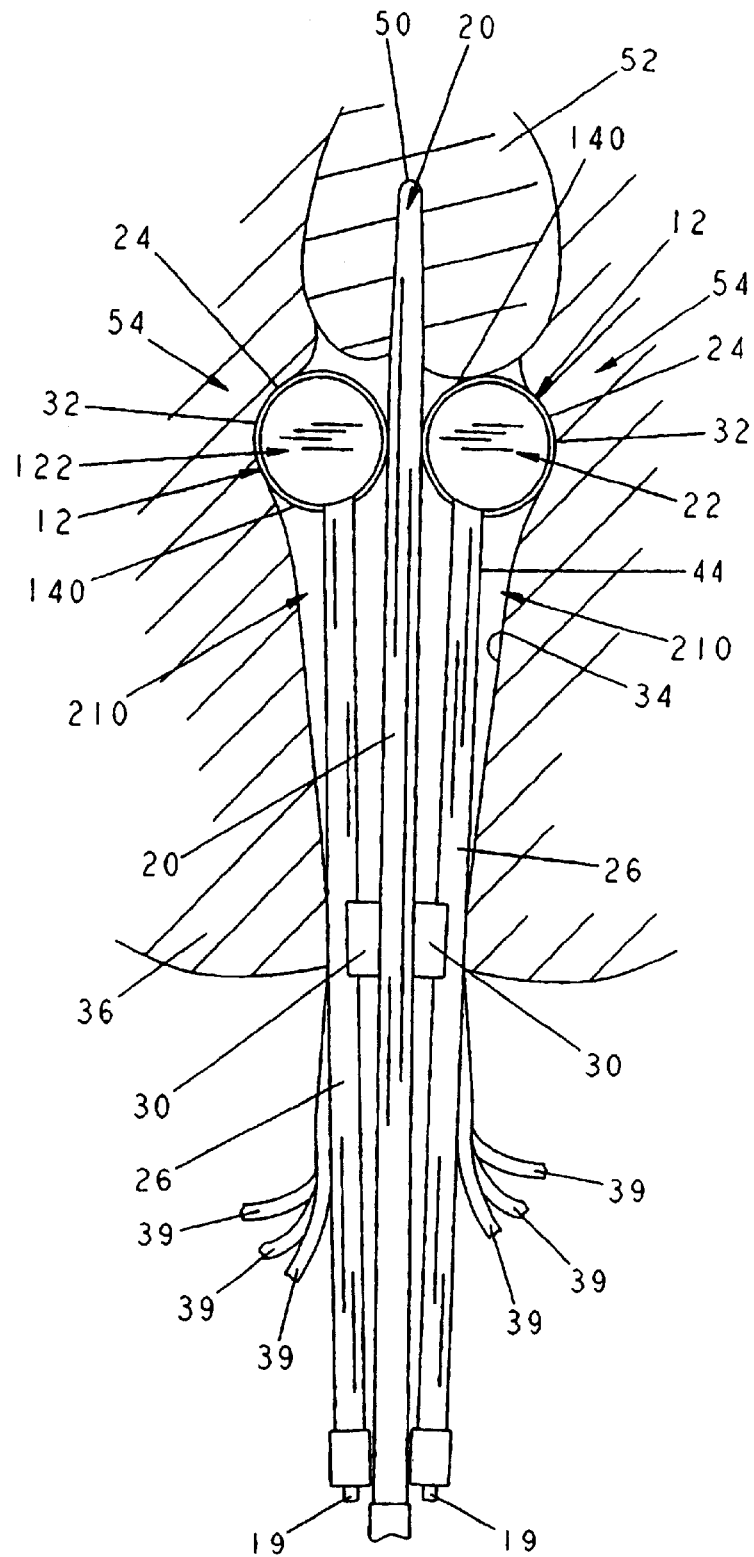
FIG. 6 is a coronal cross-sectional view of a tandem colpostat intracavitary implant and a jacket of the present invention showing the jacket coupled to the housing portion of the implant.
Figure 8:
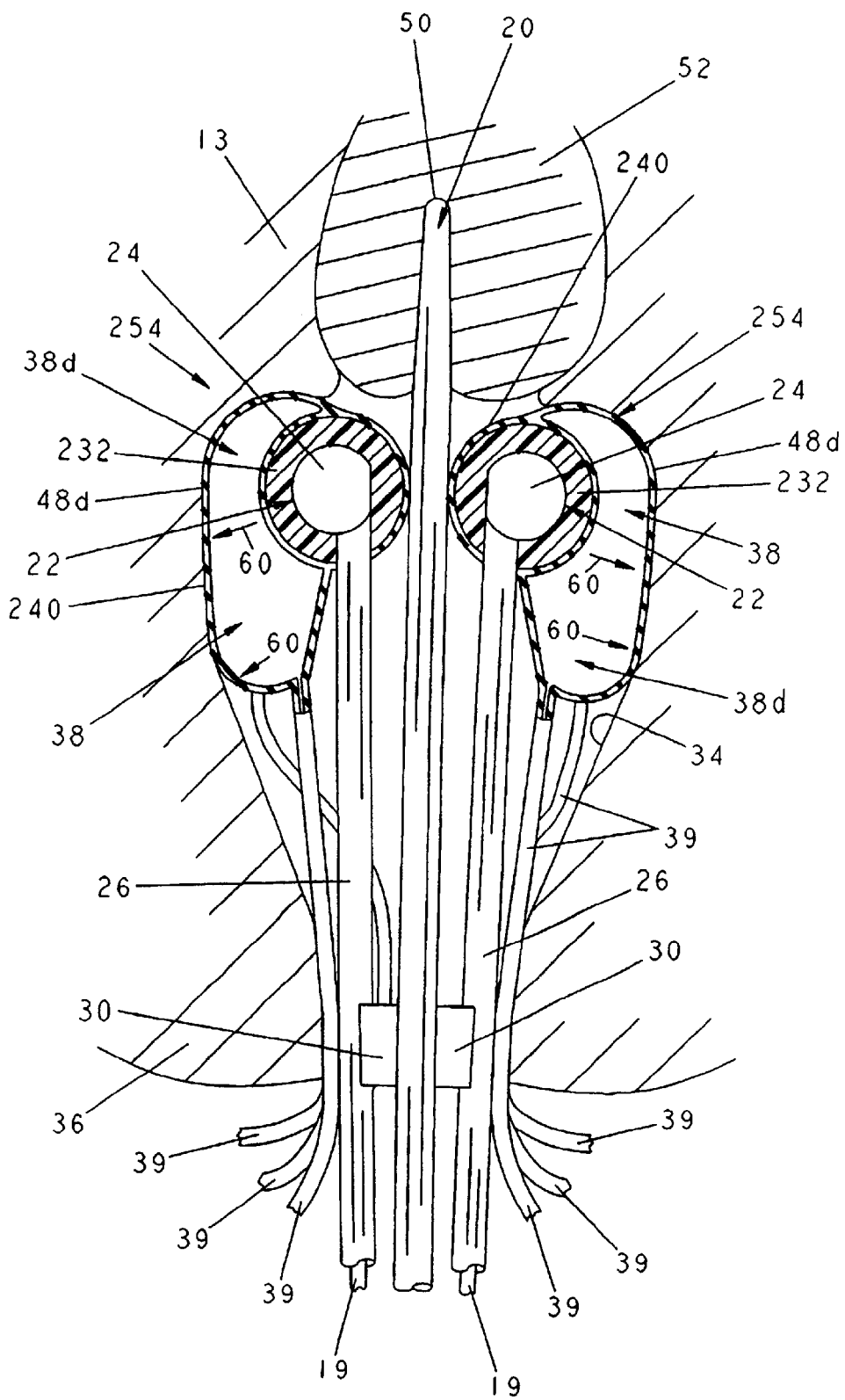
FIG. 8 is a coronal cross-sectional view of a tandem colpostat intracavitary implant, a cap coupled to the implant, and a jacket of the present invention showing the jacket coupled to the cap.

As shown in FIGS. 1 and 2, apparatus 10 includes a jacket 40 that defines a cavity 42. Jacket 40 also includes a lip 44 that defines an opening 46 into cavity 42. Opening 46 is sized to receive housing portion 24 of colpostat 22 so that housing portion 24 rests selectively within cavity 42. Housing portion 24 of colpostat 22 forms a friction-fit with jacket 40 to form a colpostat/jacket subassembly. Jacket 40 is preferably formed from a resiliently deformable plastic, radiopaque silicone, for example. Jacket 40 may also be formed from latex, pharmaceutical rubber, or any number of biocompatible expandable materials in accordance with the present invention. Although jacket 40 is coupled to colpostat 22 by a friction fit between jacket 40 and housing portion 24, it is appreciated that a wide variety of securement mechanisms such as adhesives and ties may be used to couple lip 44 on stem 26 in accordance with this disclosure. As shown in FIGS. 6 and 8, it is also appreciated that jacket 40 may be formed to be coupled to housing portion 24 or cap 32 in accordance with the present invention.

To enable apparatus 10 to selectively expand in size, apparatus 10 includes partition panels 48 that cooperate with jacket 40 to define secondary chambers 38. Chambers 38 are in fluid communication with tubes 39 that are formed to channel air into chambers 38. While air preferably is used to inflate secondary chambers 38, it is appreciated that saline with contrast medium or any number of wide varieties of fluids and gasses may be used in accordance with the present disclosure. It is also appreciated that secondary chambers 38 maybe be filled with a foam substance having a predetermined volume and selectively compressed and expanded. For example, it is appreciated that a vacuum may be pulled on the foam substance to reduce its volume, and thus the volume of the chambers 38 to a second predetermined reduced volume during implantation. The vacuum may then be reduced allowing the foam substance to expand in volume toward the first predetermined volume. The extent of expansion of the foam substance can be regulated by the amount of vacuum pulled on the secondary chambers 38.

Figure 5:
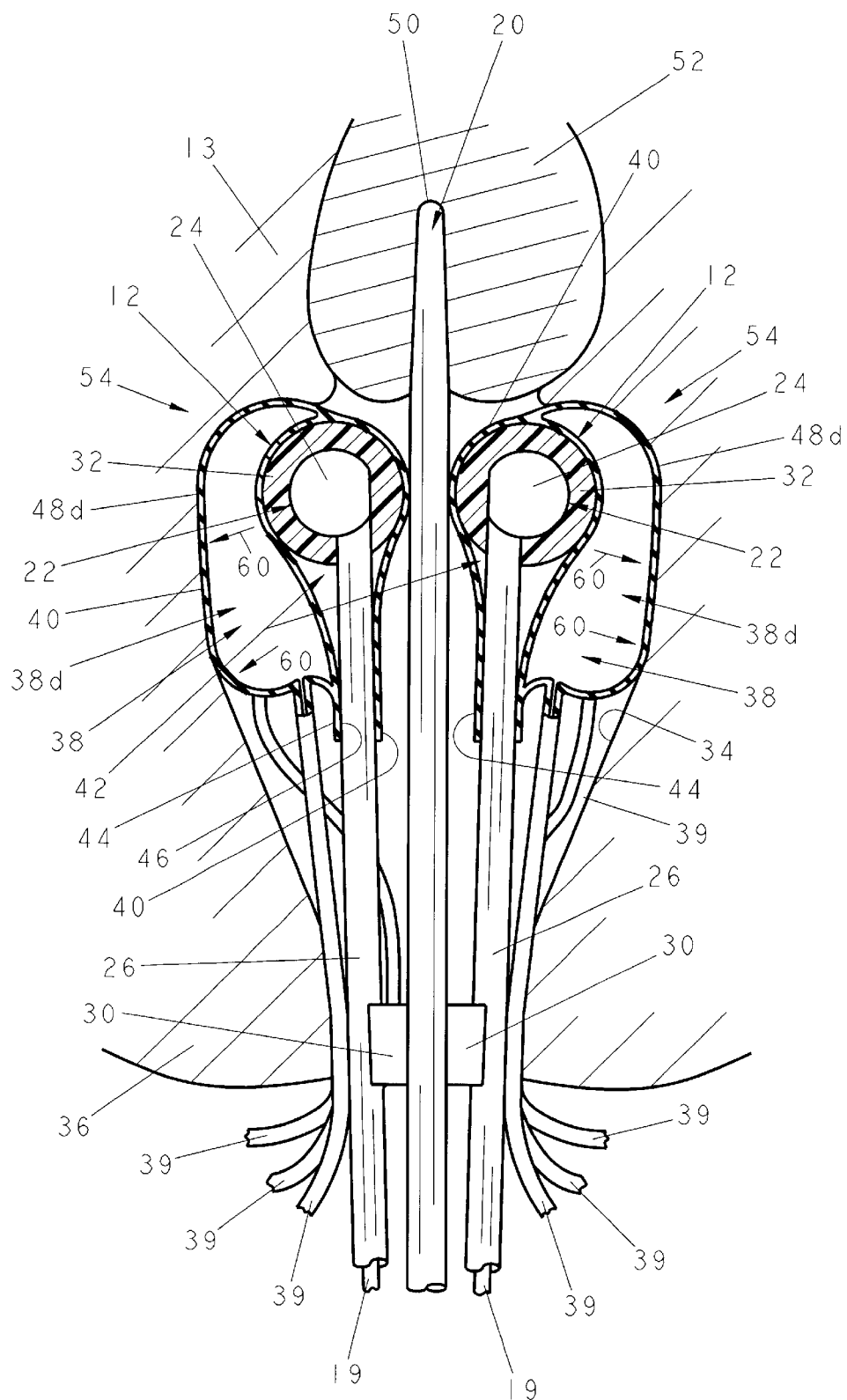
FIG. 5 is a view similar to FIG. 4 showing the secondary chambers of the dose optimization apparatuses in an inflated position to situate the colpostat in a pre-determined relationship to the tandem and to increase the percent depth dose to parmetial tissue relative to vaginal wall.

As shown in FIG. 3, anterior and posterior panels 48b, 48a are spaced-apart relative to one another and positioned for alignment with rectum 14 and bladder 16 to reduce radiation dose to rectum 14 and bladder 16. Panels 48a, 48b define anterior and posterior chambers 38b, 38a. Lateral panels 48d as shown in FIG. 5, are spaced apart relative to one another and are formed, when inflated, to selectively increase the percent depth dose to parmetial tissue 13 relative to vagina 34. Lateral panels 48d define lateral chambers 38d. Medial panels 38c, as shown in FIG. 1, of apparatuses 10 are positioned to face tandem 20. Medial panels 38c are selectively inflated and cooperate to adjust the relative positioning between colpostats 22 and tandem 20. While jacket 40 is illustrated and described, it is appreciated that jacket 40 may be formed to include greater or fewer than four partition panels 48 in accordance with the present invention. In addition, it is appreciated that chambers 38 may be formed internally within cavity 42 or within a wide variety of manners in accordance with the present invention. Jacket 40 may be formed to expand in volumetric size in predetermined positions about the housing portion of the colpostat in any number of manners in accordance with the present invention.

Figure 7:
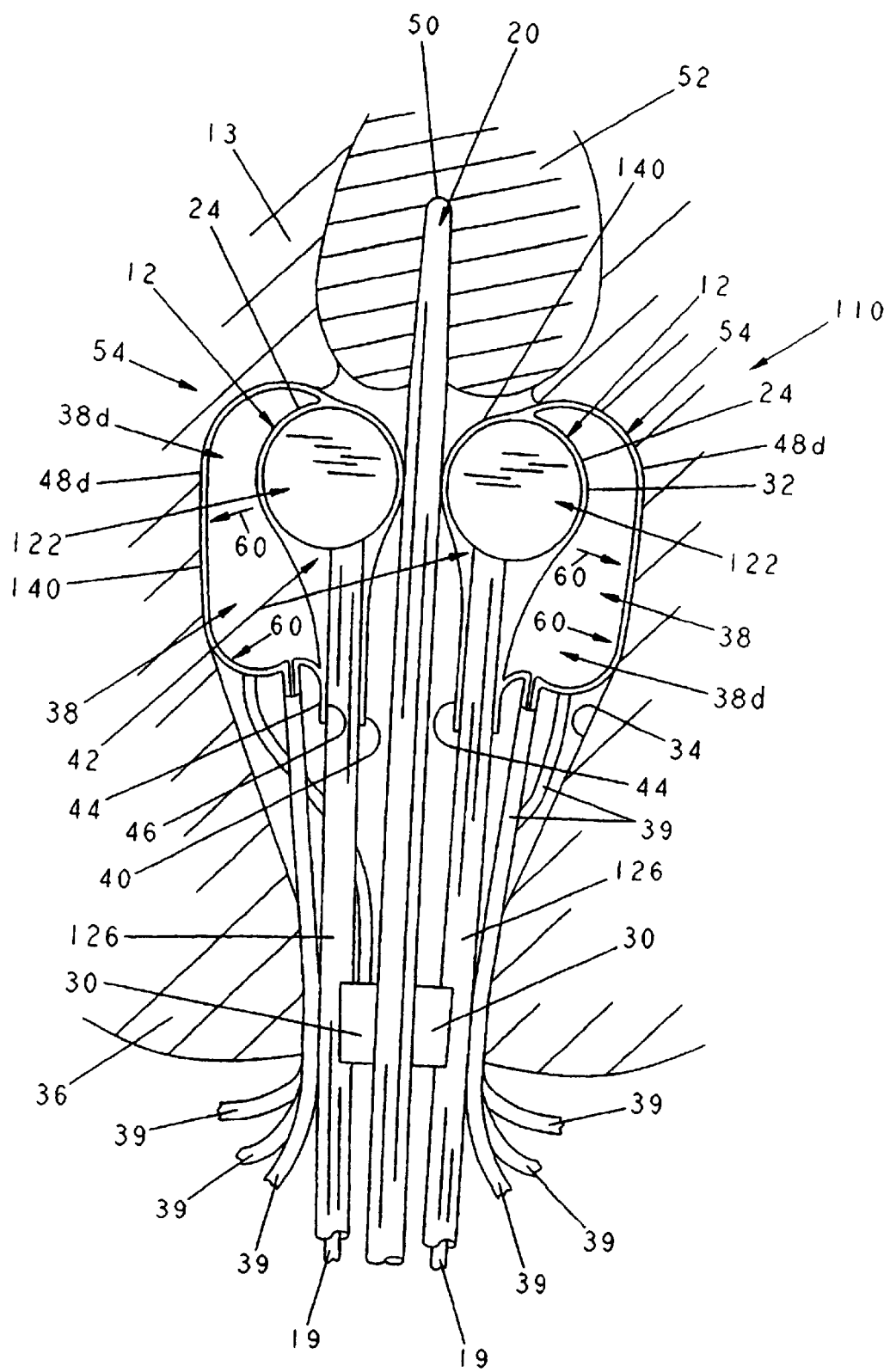
FIG. 7 is a coronal cross-sectional view of a tandem colpostat intracavitary implant and a jacket of the present invention showing the jacket coupled to the stem of the implant.

While colpostat/jacket subassembly 54 is illustrated and described, it is appreciated that jacket 40 may be formed integrally with colpostat 22 to form a one-piece apparatus 110. See FIG. 7. As used throughout the specification, like reference numerals will be used to denote like components. Specifically, in the one-piece apparatus 110, a colpostat 122 is provided in a manner similar to colpostat 22 of FIGS. 1 and 2. A jacket 140 is coupled to stem 126 during manufacturing via a friction-fit so that the physician receives the preformed disposable apparatus 110. Again, it is appreciated that jacket 140 may be coupled to colpostat 122 as discussed above with reference to jacket 40 and colpostat 22. As shown in FIG. 7, jacket 140 is formed and functions similarly to jacket 40 of FIGS. 1–5, except that it is not readily removable from colpostat 122 and preferably unit 110 is not reusable. It is appreciated that jacket 140 also may be coupled to housing portion 128 (FIG. 6) in accordance with the present invention to form a one-piece unit 210.

In addition, as shown in FIG. 8, a cap/jacket subassembly 254 is provided in accordance with the present invention. Cap 232 and jacket 240 are formed similarly to cap 32 and jacket 40 as described above. Jacket 240 is coupled to cap 232 during manufacturing via a friction-fit so that the physician receives the preformed disposable subassembly 254. It is appreciated, however, that jacket 240 may be coupled to cap 232 using an adhesive, or any number of commercially available attachment mechanisms.

In operation, the physician places pre-selected cap 32 over colpostat 22. Colpostat 22 is then inserted into opening 46 of jacket 40 until housing portion 24 rests within cavity 42 to form a colpostat/jacket subassembly 54. As shown in FIG. 2, tandem 20 is inserted into vagina 34 until an upper portion 50 of tandem 20 passes into uterus 52. Each colpostat/jacket subassembly 54 is inserted into vagina 34 and positioned to lie on opposite sides of tandem 20. In addition, jacket 40 is positioned within vagina 34 such that posterior partition 48a faces rectum 14 and anterior partition 48b faces bladder. It is appreciated that the physician may wish to adjust the positioning of the partitions 48a, 48b relative to the rectum and bladder of an individual patient.

As shown in FIG. 3, secondary chambers 38a, 38b are inflated to move partitions 48a, 48b from jacket 40, as shown by arrow 60. This movement presses vaginal wall 34 away from colpostat 22 and thus moves rectum 14 and bladder 16 away from radiation source 18. Lateral chambers 38d and medial chambers (not shown) may also be inflated, as shown by arrows 60 in FIG. 5, to increase the percent depth dose to parmetial tissue 13 relative to vagina 34 and to adjust the relative positioning between colpostats 22 and tandem 20. At this time, the physician views the positioning of the colpostat/jacket subassembly 54 via an X-ray, ultrasound, or the like to confirm the positioning of the subassembly 54 and tandem 20. Secondary chambers 38 may be inflated or deflated individually until a desired positioning of the colpostat/jacket subassembly 54 is achieved. Once the desired position is achieved, radiation sources 18 are inserted through stem and tandem 50.

When a disposable apparatus 110 is used, tandem 20 is inserted into vagina 34 until upper portion 50 of tandem 20 passes into uterus 52. Each disposable apparatus 110 is inserted into vagina 34 and positioned to lie on opposite sides of tandem 20 so that jacket 140 is aligned in a manner similar to jacket 40. Jacket 140 is inflated in a manner similar to that discussed above with reference to jacket 40 to presses vaginal wall 34 away from colpostat 122 and thus moves rectum 14 and bladder 16 away from radiation source 18

Further, when physician receives subassembly 254 in accordance with the present invention, colpostat 22 is inserted into subassembly 254. Tandem 20 is then inserted into vagina 34 until an upper portion 50 of tandem 20 passes into uterus 52. Each colpostat 22 carrying the subassembly 254 is inserted into vagina 34 and positioned to lie on opposite sides of tandem 20. Jacket 240 is then inflated as previously described with reference to jacket 40.

Although the invention has been described with reference to certain preferred embodiments, it is appreciated that variations and modifications exist within the scope and spirit of the present invention as defined by the following claims.

What is claimed is:

1. A radiation dose optimization apparatus comprising:
   a colpostat intracavitary implant including a housing portion,
   a radiation source positioned in the housing portion, and
   a jacket defining a cavity sized to receive the housing portion, the jacket being configured to selectively expand in volumetric size away from the radiation source.

2. The apparatus of claim 1, wherein the jacket is formed integrally with the colpostat.

3. The apparatus of claim 2, further comprising partitions that cooperate with the jacket to define a plurality of secondary chambers.

4. The apparatus of claim 3, further comprising tubes in fluid communication with the secondary chambers.

5. The apparatus of claim 2, wherein the colpostat includes a stem extending from the housing portion and the jacket is coupled to the stem.

6. The apparatus of claim 2, wherein the jacket is coupled to the housing portion of the colpostat.

7. The apparatus of claim 1, wherein the implant further includes a cap configured to surround the housing portion and the cap is sized for extension into the cavity of the jacket.

8. The apparatus of claim 7, wherein the cap is constructed of a plastic material.

9. The apparatus of claim 7, wherein the jacket is coupled to the cap.

10. The apparatus of claim 1, further comprising partitions that cooperate with the jacket to define a plurality of secondary chambers.

11. The apparatus of claim 10, wherein the partitions are spaced-apart relative to one another and are configured for alignment with the rectum and the bladder.

12. The apparatus of claim 10, further comprising tubes in fluid communication with the secondary chambers.

13. The apparatus of claim 1, further comprising an anterior panel, a posterior panel, and at least one lateral panel extending between the anterior and posterior panels and the anterior, posterior, and at least one later panel cooperates with the jacket to define secondary chambers.

14. The apparatus of claim 1, wherein the jacket includes a lip that defines an opening into the cavity and the opening is sized to receive the housing portion of the colpostat.

15. A radiation dose optimization apparatus comprising:
   a colpostat intracavitary implant,
   a radiation source positioned in the implant, and
   a jacket extending about at least a portion of the implant, the jacket being formed to expand in volumetric size away from the radiation source.

16. The apparatus of claim 15, wherein the jacket includes a lip that defines an opening into the cavity and the opening is sized to receive the housing portion of the colpostat.

17. The apparatus of claim 16, further comprising partitions that cooperate with the jacket to define a plurality of secondary chambers.

18. The apparatus of claim 17, wherein the partitions are spaced-apart relative to one another and are configured for alignment with the rectum and the bladder.

19. The apparatus of claim 17, further comprising tubes in fluid communication with the secondary chambers.

20. A method for optimizing radiation dose distributions to a rectum and a bladder of a patient in the treatment of malignancies of female genitalia, the method comprising the steps of:
   providing a tandem, a colpostat, radiation sources, and a jacket, the jacket defining a cavity and being configured to selectively expand in volumetric size;
   inserting the colpostat into the cavity to form a colpostat/jacket subassembly;
   inserting the tandem into a vagina of a patient until the tandem passes into a uterus;
   inserting the colpostat/jacket subassembly into the vagina adjacent to the tandem;
   inserting at least one radiation source into the tandem and into the colpostat; and
   inflating the jacket to press the wall of the vagina away from the colpostat and therefore moving the rectum and the bladder away from the radiation sources.

* * * * *